United States Patent [19]

Langham

[11] 4,282,882
[45] Aug. 11, 1981

[54] APPARATUS FOR MODIFYING INTRAOCULAR PRESSURE

[75] Inventor: Maurice E. Langham, Lutherville, Md.

[73] Assignee: Bio-Rad Laboratories, Inc., Richmond, Calif.

[21] Appl. No.: 78,842

[22] Filed: Sep. 25, 1979

Related U.S. Application Data

[63] Continuation-in-part of Ser. No. 844,076, Oct. 17, 1977, abandoned.

[51] Int. Cl.³ .............................................. A61B 5/02
[52] U.S. Cl. ................................................. 128/676
[58] Field of Search ............... 128/645, 646, 650, 676, 128/688, 297

[56] References Cited

U.S. PATENT DOCUMENTS

| | | | |
|---|---|---|---|
| 1,570,370 | 1/1926 | Brodgrsen et al. | 128/297 |
| 3,308,810 | 3/1967 | Galin | 128/676 |
| 3,911,903 | 10/1975 | Gee et al. | 128/688 |

*Primary Examiner*—William E. Kamm
*Attorney, Agent, or Firm*—Schiller & Pandiscio

[57] ABSTRACT

A cup for use with a vacuum apparatus to modify intraocular pressure by applying a distorting force to the sclera is in the form of a rigid thick-walled hollow cone with beveled base edges dimensioned to fit the curvature of the scleral surface. The inside and outside dimensions of the base are chosen to minimize patient discomfort and the potential for damage to the eye and to promote ease of application.

2 Claims, 3 Drawing Figures

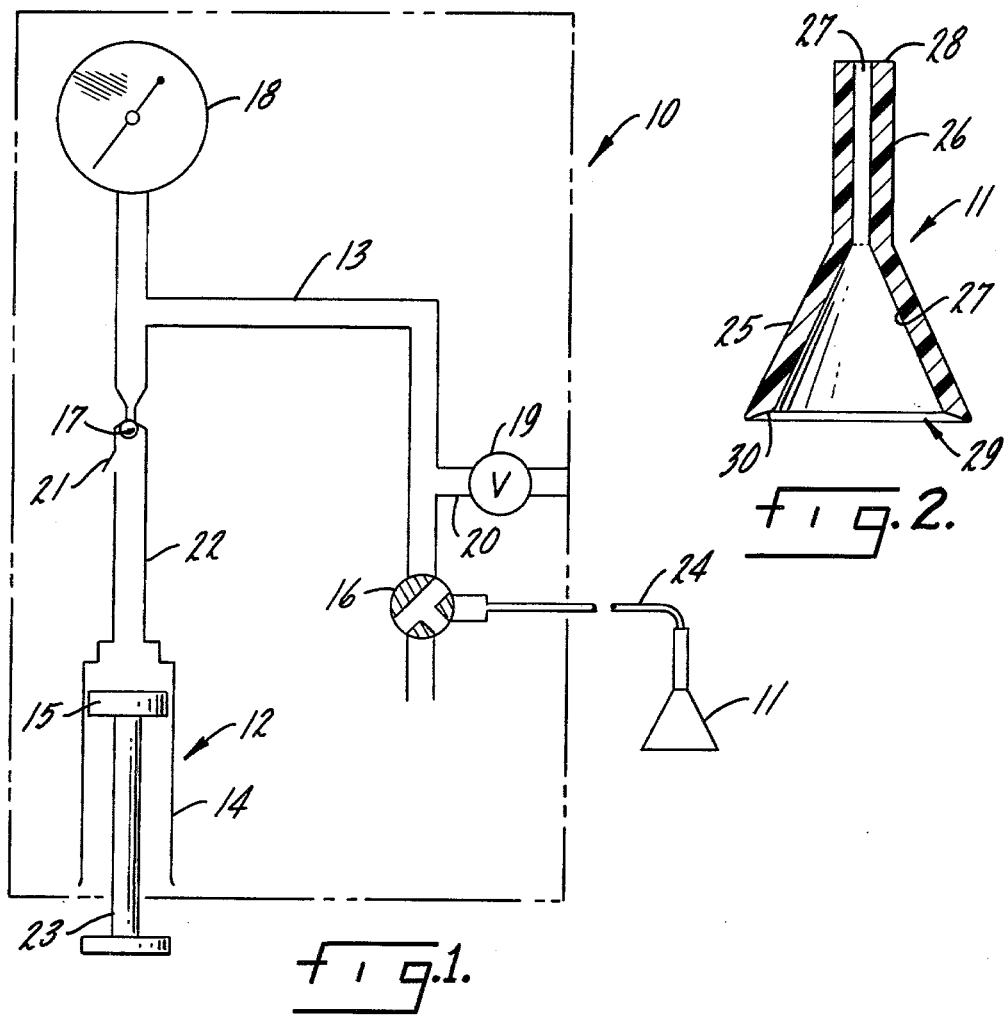
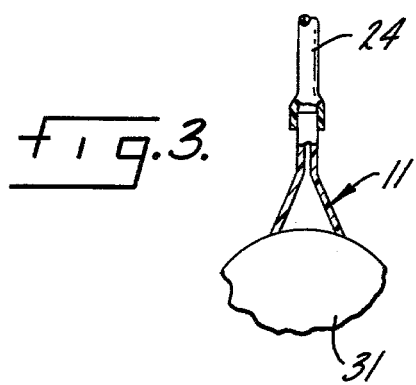

APPARATUS FOR MODIFYING INTRAOCULAR PRESSURE

This application is a continuation-in-part of copending application Ser. No. 844,076, filed Oct. 17, 1977, now abandoned.

BACKGROUND OF THE INVENTION

This invention relates to ophthalmological apparatus, and more particularly to suction cups designed to be applied to the sclera of the eye to modify, for diagnostic purposes, the intraocular pressure.

The alteration of the intraocular pressure in order to study various physiological processes in the human eye is finding increasing usefulness in research and diagnosis. Two different procedures, for different diagnostic purposes, are in common use. In the first of these, which is useful in glaucoma diagnosis, the drainage vessels which normally allow the outflow of the aqueous humor are occluded, and the subsequent pressure rise in the eye over a predetermined time interval is observed in order to determine the rate of formation of the aqueous humor. After removal of the occlusion, the rate of pressure decay in the eye can be monitored to obtain information about the aqueous humor outflow facility. Additionally, the independent measurement of the steady-state intraocular pressure, the rate of aqueous humor formation, and the outflow facility permits the calculation of venous pressure opposing the outflow of aqueous humor. Apparatus useful for carrying out this procedure typically consists of a suction cup dimensioned to fit over and clear of the cornea and provided with a flange designed to contact the perilimbal area. Partial evacuation of the suction cup results in the flange exerting a positive pressure on the perilimbal area, thereby occluding the underlying drainage vessels. An example of such a cup, and apparatus for use therewith, is disclosed in U.S. Pat. No. 3,308,810.

In the second procedure, useful in the detection of carotid artery occlusive disease, a suction cup is applied above the sclera of the patient's eye clear of the area of the cornea. Partial evacuation of the cup results in the physical deformation of the eye which in turn raises the intraocular pressure. Observation of the pulse of the ophthalmic artery as a function of varying intraocular pressure permits the evaluation of the ophthalmic arterial pressure in conscious human subjects. Prior art procedure typically employs apparatus such as that disclosed in U.S. Pat. No. 3,308,810, together with an observation of ocular pulse through, for instance, observations of the fundus, or employs similar suction cups in an apparatus incorporating pneumatic sensing of the applied vacuum, as in U.S. Pat. No. 3,911,903.

Practical considerations in the design of the perilimbal-type cup result in a more or less thin-walled bell-shaped cup having a broad external flexible flange, this shape providing corneal clearance and also insuring that the flange of the cup, by conforming to the shape of the eye, seals the cup to the perilimbal region, part of which is normally covered by the eyelids, with a minimal amount of patient discomfort. The flexible flange and thin-walled cup further allow a reasonably high external pressure to be locally applied to the perilimbal region with minimal negative pressure inside the cup.

Although commonly used for the second procedure, perilimbal cups, because of their shape and size, suffer from a number of disadvantages. For example, the force necessary to distort the eye to raise the intraocular pressure to that of the ophthalmic artery may result in too high an external pressure being placed on the conjunctiva by such a cup, with damage possibly occuring as a result. Further, in applying a suction cup above the sclera of the eye clear of the area of the cornea, the cup is applied to one, typically the temporal, side of the eye, while the patient is instructed to look in the opposite direction. It will be appreciated that such a location of a perilimbal cup, because of its size, results in an even greater displacement of the eyelids, with a substantially greater portion of the flange disposed under the lid and the lid partially retracted by the bell of the cup. Not only does this increase the amount of patient discomfort, but experimentally such a situation should be avoided, as the resultant forces exerted on the cup by the eyelids, being uncontrolled, are a potential source of error. Additionally, for some procedures, it is desirable that the patient fixate straight ahead during measurements; the perilimbal type cups again because of their size require the patient to gaze nasally, thereby preventing forward fixation. This also may place a distrubing stress on the external rectus. Further, the size of the perilimbal cup results in a cup of substantial mass which, by applying a torque on the eye, may indirectly lead to muscular forces of unknown magnitude being placed on the eye in an attempt by the musculature to overcome the torque. Finally, the bell-shaped cup is difficult to handle, in that its abruptly changing diameter offers essentially a choice, for a grip, of either a small diameter stem remote from, or a large diameter bell near to, the eye.

A reduction in the size of the cup is clearly desirable. However, it will be recongized that any reduction in the inside diameter of the cup results in the vacuum producing the distortional force being deployed over a smaller area, which in turn requires that a larger vacuum be employed to produce a given intraocular pressure. Further, it will be recognized that any reduction in flange area results in a greater force per unit area being exerted on the eye. Both can lead to eye damage. At too great a negative pressure differential, it is possible to rupture the capillaries underlying the center of the cup. Too small a contact surface may lead to cutting the conjunctiva with the edge of the cup when distorting forces are applied.

OBJECTS OF THE INVENTION

Accordingly, it is an object of the present invention to provide an ocular suction cup suitable for applying a distorting force on the eye so as to increase the intraocular pressure beyond that of the ophthalmic arterial pressure without damage to the conjunctiva or underlying tissue and without discomfort to the patient.

Further, it is an object of the present invention to provide an ocular suction cup of a new design which is also smaller and lighter in weight than prior art ocular suction cups.

An additional object is to provide a cup of a shape which is easy for the practitioner to handle and apply.

BRIEF SUMMARY OF THE INVENTION

These and other objects are met in the present invention of a cup for use with a vacuum apparatus to modify intraocular pressure by applying a distorting force to the sclera wherein the cup is in the form of a rigid thick-walled hollow cone with beveled base edges dimensioned to fit the curvature of the scleral surface. The inside and outside dimensions of the base are chosen to maximize the area of the scleral portion subjected to the vacuum while minimizing the contact pressure (i.e. force per unit area) between the base edges and the scleral portion, thus minimizing the potential for damage to the eye, patient discomfort, and the effects of spurious forces, as well as promoting ease of application.

The substitution of a rigid, thick, beveled edge for a broad flexible flange results in a better distribution of force over the area of contact between cup and sclera, thereby minimizing the potential for damage to the eye. This in turn allows the use of a smaller diameter cup, with consequent greater patient comfort, and by allowing forward fixation without contacting the eyelids, better experimental control. It will be appreciated that the smaller diameter cup can also be lighter in weight than prior art cups. Finally, the conical shape of the cup, due to its gradually tapering contour, is more easily handled than is a bell-shaped cup.

Other objects of the present invention will in part be obvious and will in part appear hereinafter. The invention accordingly comprises the apparatus possessing the construction, and arrangement of parts exemplified in the following detailed disclosure, the scope of the application of which will be indicated in the claims.

BRIEF DESCRIPTION OF THE DRAWINGS

For a fuller understanding of the nature and objects of the present invention, reference should be had to the following detailed description taken in connection with the drawings wherein:

FIG. 1 is a schematic plan view of an apparatus embodying the present invention;

FIG. 2 is an enlarged sectional elevation of a scleral cup embodying this invention; and FIG. 3 is an elevational view, partly broken away, showing the scleral cup applied to the sclera of an eye.

In the several views, like numbers are used to designate like parts.

DESCRIPTION OF PREFERRED EMBODIMENTS

Referring to FIG. 1, apparatus 10 includes scleral cup 11 that communicates with negative pressure source 12 via conduit or confined flow passageway 13. Negative pressure source 12 can be a pump such as a syringe having barrel 14 within which is received a reciprocating plunger 15 actuated by means of plunger rod 23. Alternatively, negative pressure source 12 can be a power-driven vacuum pump or a similar device. Three-way valve 16 is provided in conduit 13 between scleral cup 11 and negative pressure source 12, as well as check valve 17 which permits the maintaining of a predetermined negative pressure within conduit 13 and scleral cup 11 when the latter is applied to the eye of a patient.

Negative pressure indicator 18, such as a vacuum gauge or the like, is operably associated with conduit 13 so as to give an indication of negative pressure within scleral cup 11. Alternatively, indicator 18 can be a pressure transducer associated with a transcriber. Pressure release valve 19 is provided in auxiliary conduit 20 which permits communication between conduit 13 and ambient atmosphere. In this manner, when valve 19 is opened, negative pressure within conduit 13 and within scleral cup 11 applied to the eye of a patient can be vented to the atmosphere, i.e., released. Preferably pressure release valve 19 is a needle valve or the like that permits a controlled release of the negative pressure at a desired rate over an extended period of time.

Three-way valve 16 is optional but desirable in that additional flexibility is imparted to the present apparatus. For instance, valve 16 can be used to hold negative pressure within scleral cup 11 after the latter has been applied to the eye of a patient by closing off communication with main conduit 13. Also, with valve 16 closed, negative pressure can be built up within that portion of conduit 13 defined by valve 16 and check valve 17 to a desired value before any negative pressure is applied to the eye through scleral cup 11. Three-way valve 16 additionally can serve as a rapid pressure release valve, if desired.

Check valve 17 facilitates the maintenance of negative pressure within conduit 13 and also permits the build-up of greater negative pressure within conduit 13 by moving plunger or piston 15 through a plurality of reciprocating strokes. In order to release the positive pressure generated by plunger 15 within barrel or bore 14 and against check valve 17 during a compression stroke, pressure relief valve 21 is provided in conduit 13 between check valve 17 and plunger or piston 15. Pressure relief valve 21 can be a conventional flapper valve or reed valve, or can be associated with plunger 15 in any other operable manner to provide pressure relief during the compression stroke, e.g., by being built into plunger 15 instead of being mounted on end segment 22 of conduit 13.

To facilitate manipulation and use of scleral cup 11, distal end segment 24 of conduit 13 preferably is flexible, for example, a piece of flexible tubing.

The preferred configuration of scleral cup 11 is illustrated in FIG. 2. Scleral cup 11 preferably is a hollow housing or member including conical head portion 25 with rim 29 formed in an edge of the wall defining the head portion, defining a circular opening or mouth of cup 11 that is adapted to be placed on the sclera of an eye and hollow stem portion 26 unitary with hed portion 25. Usually stem portion 26 is cylindrical and distal end 28 thereof is adapted for connection to flexible end segment 24 of conduit 13. Head portion 25 at the apex merges into stem portion 26 and portions 25 and 26 together define central through passageway 27 by means of which the negative pressure generated within conduit 13 is transmitted to the eye that is being studied.

Rim 29 is rounded and has peripheral surface 30 beveled inwardly for optimum contact with but minimal contact on the eye when scleral cup 11 is in use. Preferably the height of the conical head portion is about the same as the diameter of central through passageway 27 at the base of conical head portion 25.

The shape and size of scleral cup 11 is selected on the basis of its efficacy to efficiently increase intraocular pressure while minimizing the potential for damage to the sclera, patient discomfort, and the effects of spurious forces, as well as for its ease of application. In this regard, it is desirable to maximize the force that can be applied to the eye by a given, preferably relatively soft partial vacuum (relatively low negative relative pressure), in order to avoid damage to the portion of the eye experiencing the vacuum. To this end, it is preferable to maximize the ratio of the area enclosed by rim 29 over which the negative pressure can be applied to the area of contact between the rim and the sclera. At the same time, it is desirable to minimize the contact pressure between rim 29 and the sclera produced by this force, in order to avoid damage to the conjunctiva and sclera contacted by the rim. Further, to aid in ease of attachment, increase patient comfort, minimize spurious effects arising from interaction of the cup with the eyelids, and permit forward fixation, the cup should have an outside diameter at the base of conical head section 25 corresponding to the spherical segment of the sclera of the forward fixated in vivo human eye which is readily accessable. Inasmuch as there is variation in the dimensions of eyes, it will be readily understood by persons skilled in the art that as a practical matter these conditions cannot be met exactly using a singlesized eye cup. These competing requirements can be substantially met in the case of the human eye with a cup having a diameter of between 9 and 10 millimeters as the inside dimension at the base of conical head section 25 and a diameter of about 13 millimeters as the outside dimension (i.e., a cup having an outside diameter of about 13 millimeters and a wall thickness on the order of 1.5 to 2.0 millimeters). For such a cup, the scleral contact surface, rim 29, should be beveled inwards to have a concave radius of curvature of about 13 millimeters in order to optimally minimize contact pressure.

The material of construction for scleral cup 11 is not overly critical and can be metal or plastic. A particularly preferred material of construction is a transparent acrylic resin such as those commercially available from E. I. duPont de Nemours & Co. of Wilmington, Del., under the designation "Lucite".

Use of the apparatus of the present invention is illustrated in FIG. 3 where scleral cup 11 is shown applied to sclera 31. Initially, valves 16 and 19 (FIG. 1) are closed and negative pressure within conduit 13 is built up to an intermediate value of the order of about 50 to 75 mm Hg. Cup 11 is then applied to sclera 31 and valve 16 is opened to transmit the negative pressure to the eye. As a result, cup 11 is held in place by the negative pressure which can then be adjusted to the desired value while other measurements, e.g., intraocular pressure and pulse, are being made. After the desired measurements have been completed, the negative pressure within cup 11 and conduit 13 is vented to ambient atmosphere by opening needle valve 19 (and/or valve 16). When the pressure within cup 11 reaches about atmospheric, cup 11 is removed from sclera 31 by simply lifting cup 11 off the eye.

The foregoing specification and accompanying drawings are intended as illustrative and are not to be taken as limiting. Still other variations, modifications, and rearrangements of parts within the spirit and scope of this invention are possible and will readily present themselves to those skilled in the art.

What is claimed is:

1. In an apparatus for modifying intraocular pressure in an eye by applying a negative pressure to a scleral portion of said eye, said apparatus including a hollow, scleral cup means intended to be applied to said scleral portion and a valved conduit extending into said cup for withdrawing gas from said cup to create said negative pressure, said cup means having an open portion defined by rigid thick walls the interior periphery of which defines the area of said scleral portion subjected to said negative pressure upon application of said cup means to said scleral portion, the improvement wherein the surface of said cup means intended to contact said scleral portion is an edge of said rigid thick walls, said edge being beveled inwardly with a concave radius of curvature.

2. Apparatus as defined in claim 1 wherein said radius of curvature is about 13 millimeters and wherein said open portion is of circular section and has an inside diameter of between 9 and 10 millimeters, and wherein said rigid, thick walls have a thickness of about 1.5 millimeters at said surface.

* * * * *